(12) United States Patent
Frappier et al.

(10) Patent No.: US 11,369,507 B2
(45) Date of Patent: Jun. 28, 2022

(54) METHOD AND DEVICE FOR POSITIONING A LIMB

(71) Applicants: Debra Ann Frappier, Scappoose, OR (US); Dennis Frappier, Scappoose, OR (US)

(72) Inventors: Debra Ann Frappier, Scappoose, OR (US); Dennis Frappier, Scappoose, OR (US)

(*) Notice: Subject to any disclaimer, the term of this patent is extended or adjusted under 35 U.S.C. 154(b) by 146 days.

(21) Appl. No.: 16/436,815

(22) Filed: Jun. 10, 2019

(65) Prior Publication Data

US 2020/0383817 A1 Dec. 10, 2020

(51) Int. Cl.
*A61F 5/37* (2006.01)
*A61F 5/058* (2006.01)

(52) U.S. Cl.
CPC .......... *A61F 5/3761* (2013.01); *A61F 5/0585* (2013.01)

(58) Field of Classification Search
CPC ........ A61F 5/3761; A61F 5/01; A61F 5/0111; A61F 5/0113; A61F 5/0116; A61F 13/041; A61F 13/043; A61F 5/05841; A61F 5/0585; A61H 3/00; A61H 1/0237; A61H 1/0255; A61H 2201/1635; A61H 2201/1638; A61H 2201/164; A61H 2201/1642; A61H 2201/165; A61H 2201/1269; A61H 2203/0431; A61H 2203/0437; A61H 2203/0425; A45B 3/04; A61G 7/1023
USPC ............. 128/845, 882; 602/5, 23, 28; 601/5; 135/65–86
See application file for complete search history.

(56) References Cited

U.S. PATENT DOCUMENTS

| | | | | |
|---|---|---|---|---|
| 4,019,503 A | * | 4/1977 | Smith | A61F 13/045 602/11 |
| 4,599,996 A | * | 7/1986 | Seith | A61F 13/041 482/51 |
| 4,790,339 A | * | 12/1988 | Bennett | A45B 7/00 135/65 |
| 4,854,313 A | * | 8/1989 | Kloepper | A61F 5/37 128/882 |
| 6,004,282 A | | 12/1999 | Whitley | |
| 8,087,707 B1 | * | 1/2012 | Hawkins | A47G 25/90 294/24 |
| 9,314,920 B1 | * | 4/2016 | Jutras, Jr. | F21V 33/0084 |
| 2006/0124162 A1 | * | 6/2006 | Sweeney | A63B 21/0552 135/65 |

(Continued)

OTHER PUBLICATIONS

"Performance Health/SammonsPreston Rigid Leg Lifter" https://www.performancehealth.com/rigid-leg-lifter.

*Primary Examiner* — Rachael E Bredefeld
*Assistant Examiner* — Trisha Talapatra
(74) *Attorney, Agent, or Firm* — Scott R. Hansen; Viking IP Law

(57) ABSTRACT

A patient grasps a handle grip of a repositioning device. The patient may be on a bed or a couch, for example, and wishes to pull the injured limb up onto the bed or couch without having to bend over. The device has a shaft, a handle grip on a proximal end of the shaft and a hook on a distal end of the shaft. The patient secures the hook to something that is about the limb, such as a cast, brace, bandage, or the like. Once the hook is secured, the user pulls the device upwardly to raise the limb. Once the user has positioned the limb as desired, the hook is disengaged.

7 Claims, 8 Drawing Sheets

(56) References Cited

U.S. PATENT DOCUMENTS

| | | | |
|---|---|---|---|
| 2009/0170671 A1* | 7/2009 | Faktenmark | A63B 21/0004 |
| | | | 482/122 |
| 2011/0166485 A1* | 7/2011 | Owens | A61H 1/0237 |
| | | | 601/5 |
| 2013/0141899 A1* | 6/2013 | Lee | A45B 3/04 |
| | | | 362/102 |
| 2014/0041702 A1* | 2/2014 | Yamamoto | A45B 9/02 |
| | | | 135/77 |
| 2016/0074198 A1* | 3/2016 | Wada | A61F 5/0113 |
| | | | 602/27 |
| 2019/0275369 A1* | 9/2019 | Beddoe | A63B 21/4039 |

* cited by examiner

METHOD AND DEVICE FOR POSITIONING A LIMB

TECHNICAL FIELD OF THE INVENTION

The present invention relates to a device for positioning a limb, such as for moving an injured limb up or down, or side-to-side.

BACKGROUND

Millions of people globally have limited leg mobility. This can occur from injuries or surgery, including knee and hip replacement surgery, arthritis, and/or immobility as from stroke. Also, a leg may become tired from overuse.

Often, one needs assistance getting into or out of chairs, wheelchairs, beds or cars, for example. It is important to be able to conveniently pull and lift the leg or cast into position. Physical therapists may need to aid patients through exercise, such as by working the muscles in their limbs during recovery by performing and with light stretching.

It would meet a need to provide an improved limb positioning device to aid in positioning the limb without the user needing to bend over. The device should accommodate a range of limb sizes, casts, or braces.

BRIEF SUMMARY

One method according to the present invention relates to repositioning a limb of a patient. A user grasps a handle grip of a repositioning device. The device has a shaft, a handle grip on a proximal end of the shaft and a hook on a distal end of the shaft. The user secures the hook to something that is secured to the limb, such as a cast, brace, bandage, boot or the like. Once the hook is secured, the user pulls the device upwardly to raise the limb. The user may be on a bed or a couch, for example, and wishes to pull the injured limb up onto the bed or couch without having to bend over. Once the user has positioned the limb as desired, the hook is disengaged.

Various steps and/or featured may be incorporated, either alone or individually in various embodiments. For example, the shaft may be linear or non-linear (such as curved). It may have a cylindrical cross-section, or any of a variety of cross-sections, and be hollow or solid. The hook may be secured onto a portion of a frame, loop, or other portion of cast, brace, bandage, or the like. The method may be performed by the user themself, by another person, or a combination of the two. The device may have one or more additional features, such as a wrist strap to help keep the device attached to the user. The grip may be a bicycle-style grip that is resilient and/or non-slip.

The length of the device is typically fixed. But some embodiments may include a shaft that is variable in length. In one example, the shaft is telescoping and the user adjusts the length as desired then locks the length into place. The device might also include, for example, a light source such as an LED that the user may activate at night to better illuminate the area to be hooked. The LED may be interconnected to a button on the handle, for example, such that the user may switch it on and off.

In another embodiment, a method of repositioning a limb of a patient has steps of grasping a handle grip of a repositioning device, the device comprising a shaft, a resilient non-slip handle grip on a proximal end of the shaft, a hook on a distal end of the shaft, and a film over at least a portion of the shaft. A hook is secured such that movement of the shaft moves the limb. The limb is positioned into a desired position, and the hook disengaged to leave the limb in the desired position.

Again, the disclosed concepts include variations, and the optional features noted above may be added to embodiments of the invention, either alone or in various combinations as appropriate.

A further understanding of the nature and advantages will become apparent by reference to the remaining portions of the specification and drawings.

DETAILED DESCRIPTION

Figure 1:
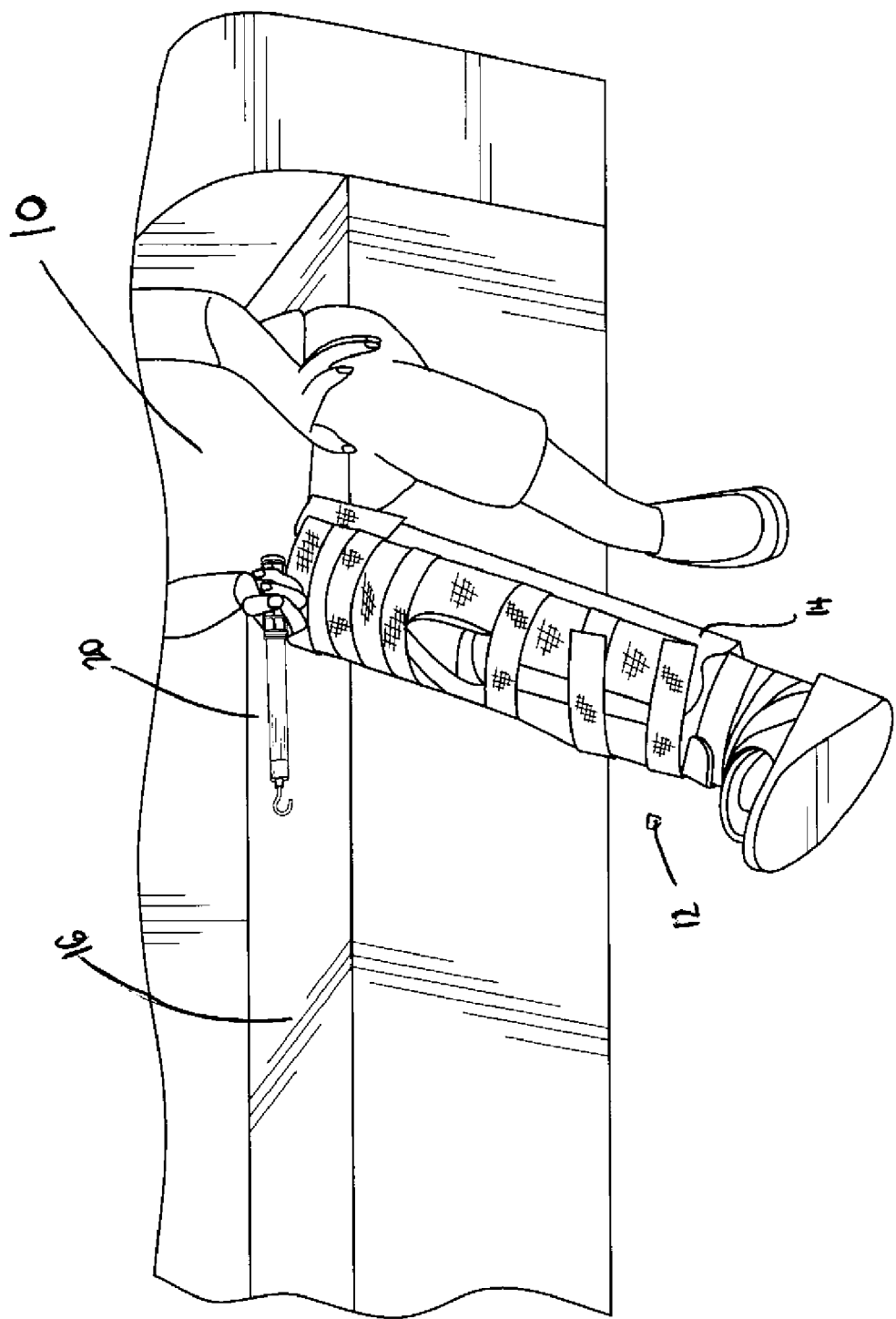
FIG. 1 illustrates a patient sitting on a couch with an immobile leg in a cast.
Figure 6:
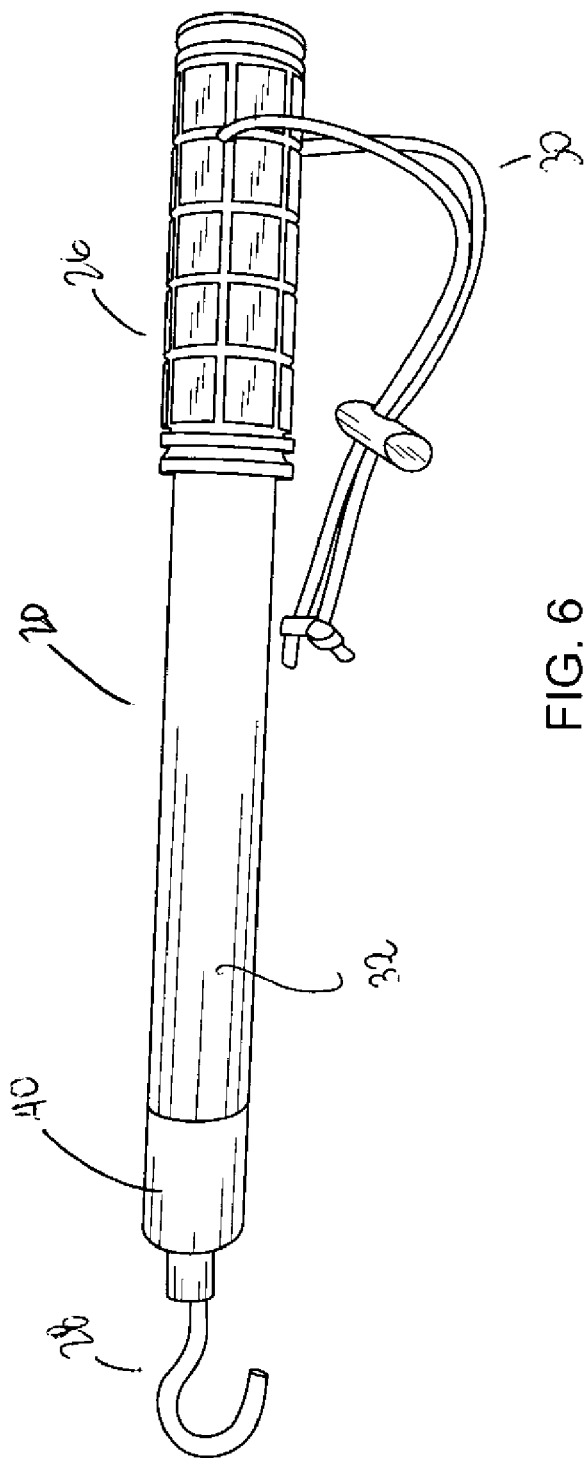
FIG. 6 illustrates a device according to the present invention.
Figure 7:
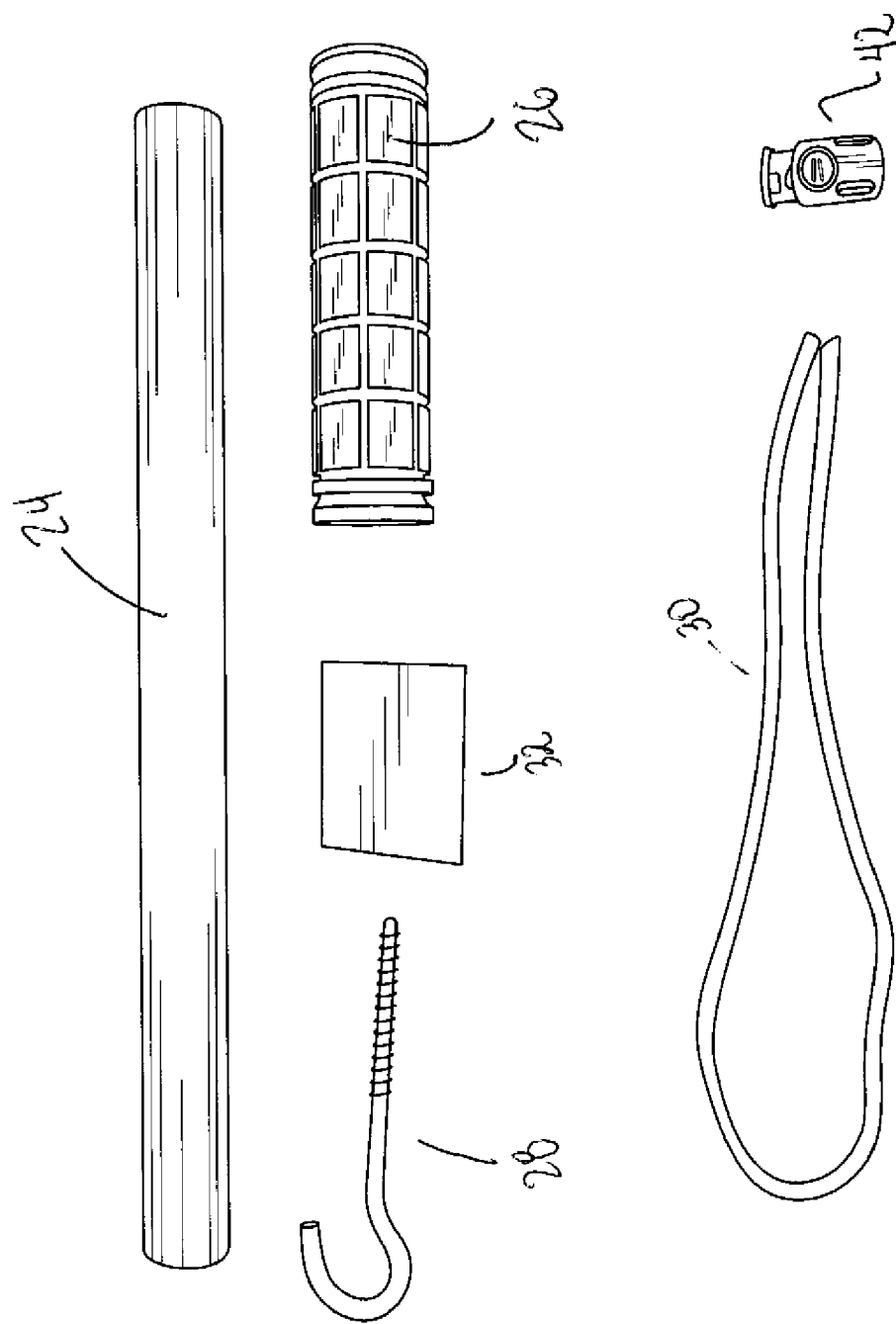
FIG. 7 illustrates components of an embodiment of the present invention, including such components as a shaft, hook, and handle grip.

Considering presently preferred embodiments with reference to the drawings, FIG. 1 illustrates a patient 10 with an injured leg 12 in a cast 14. The patient is sitting on a couch, for example, and wishes to raise her leg onto the couch 16 without having to bend over to any significant extent. The east 14 has various straps on it, as well as other structures onto which a repositioning hook may be attached. It also has a hoot. The user is holding a positioning device 20 in her right hand. The device 20 includes a shaft 24, a grip 26 on a proximal end of the shaft, and a hook 28 on the distal end of the shaft (FIGS. 6, 7). The device may also include an adjustable wrist strap 30, as well as a film such as shrink wrap 32 that has a decorative color and/or pattern.

Figure 2:
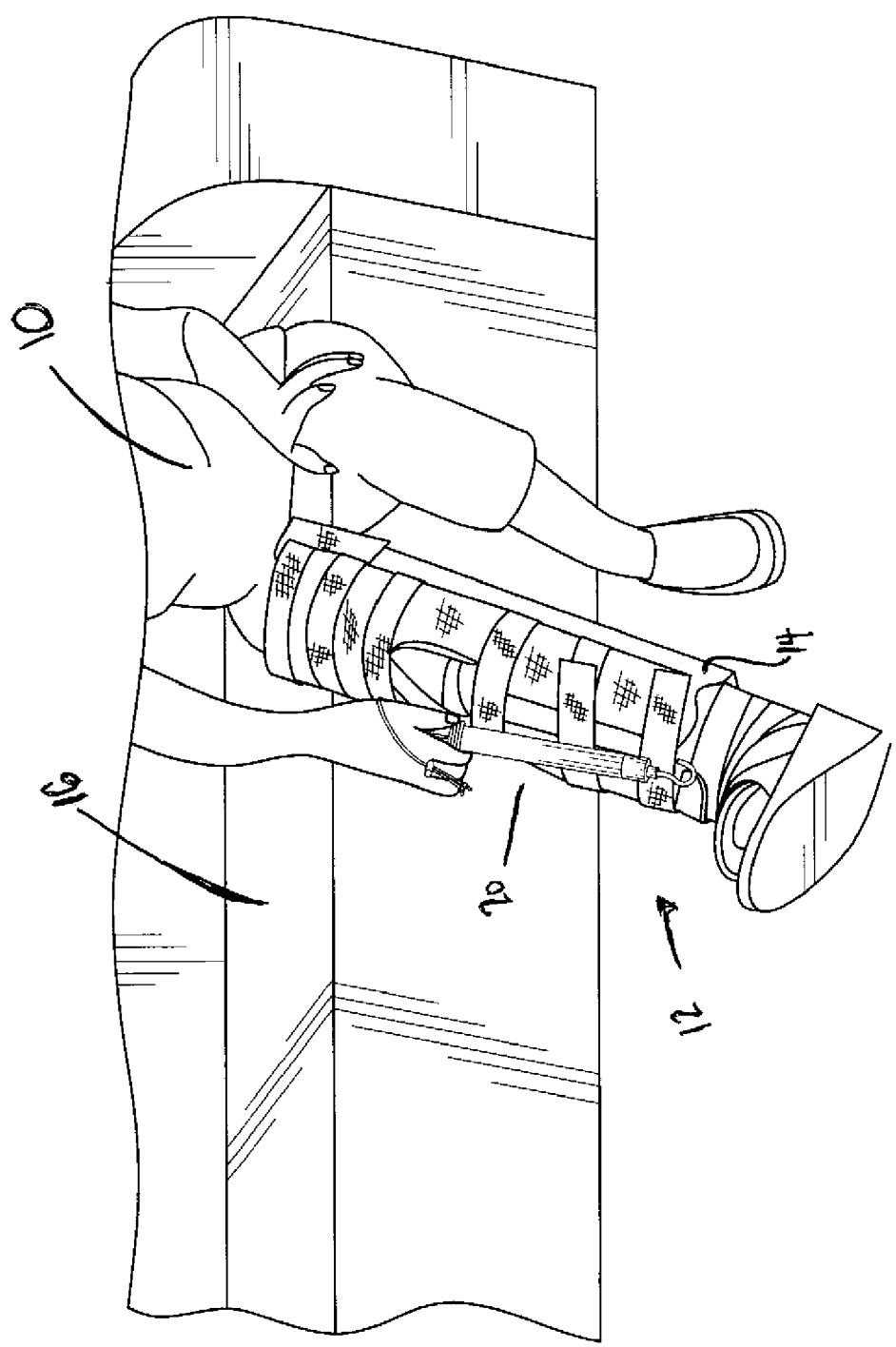
FIG. 2 illustrates grasping a portion of the cast with a hook of a device according to the present invention
Figure 3:
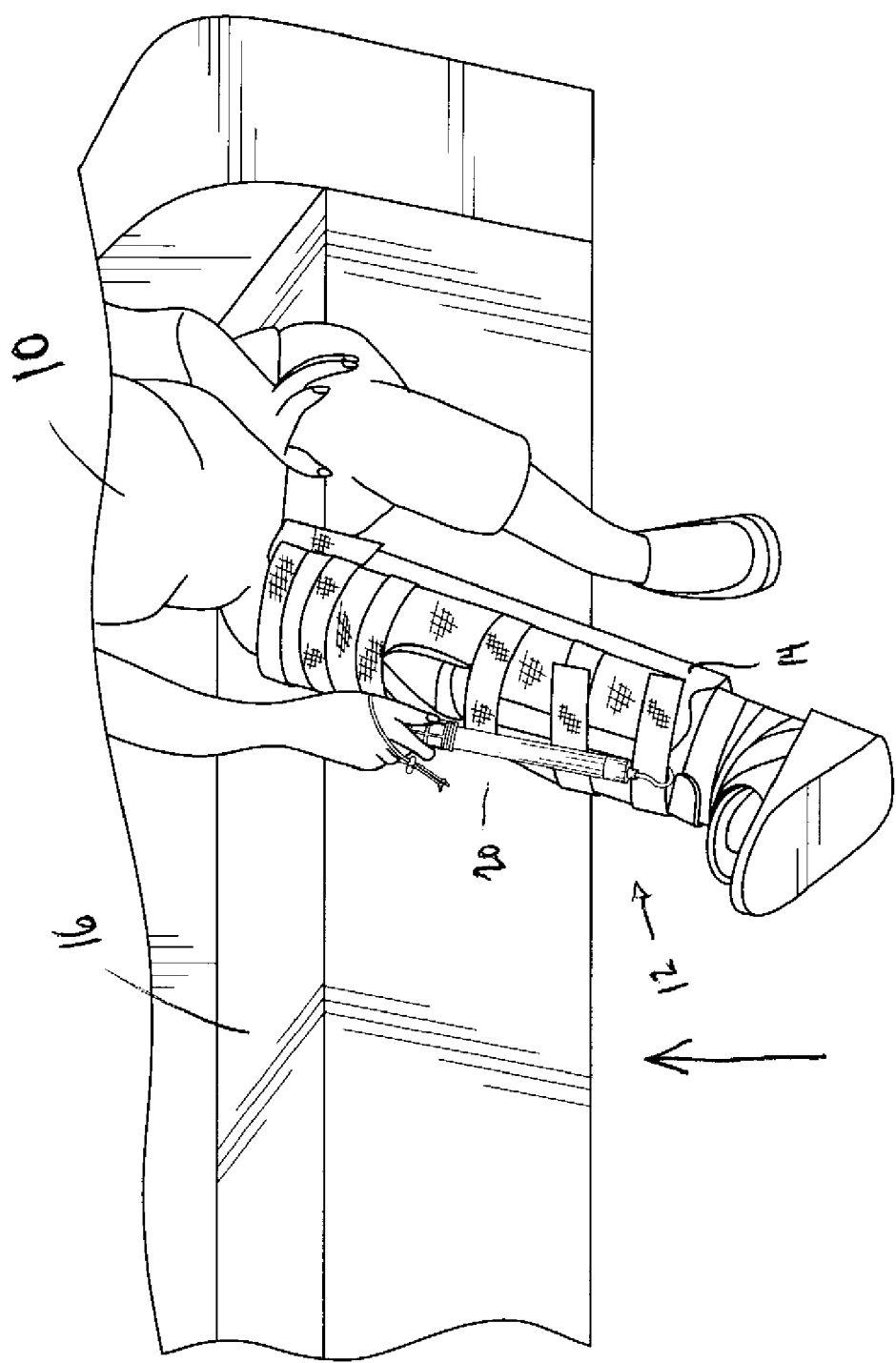
FIG. 3 illustrates pulling up on the cast with the device.
Figure 4:
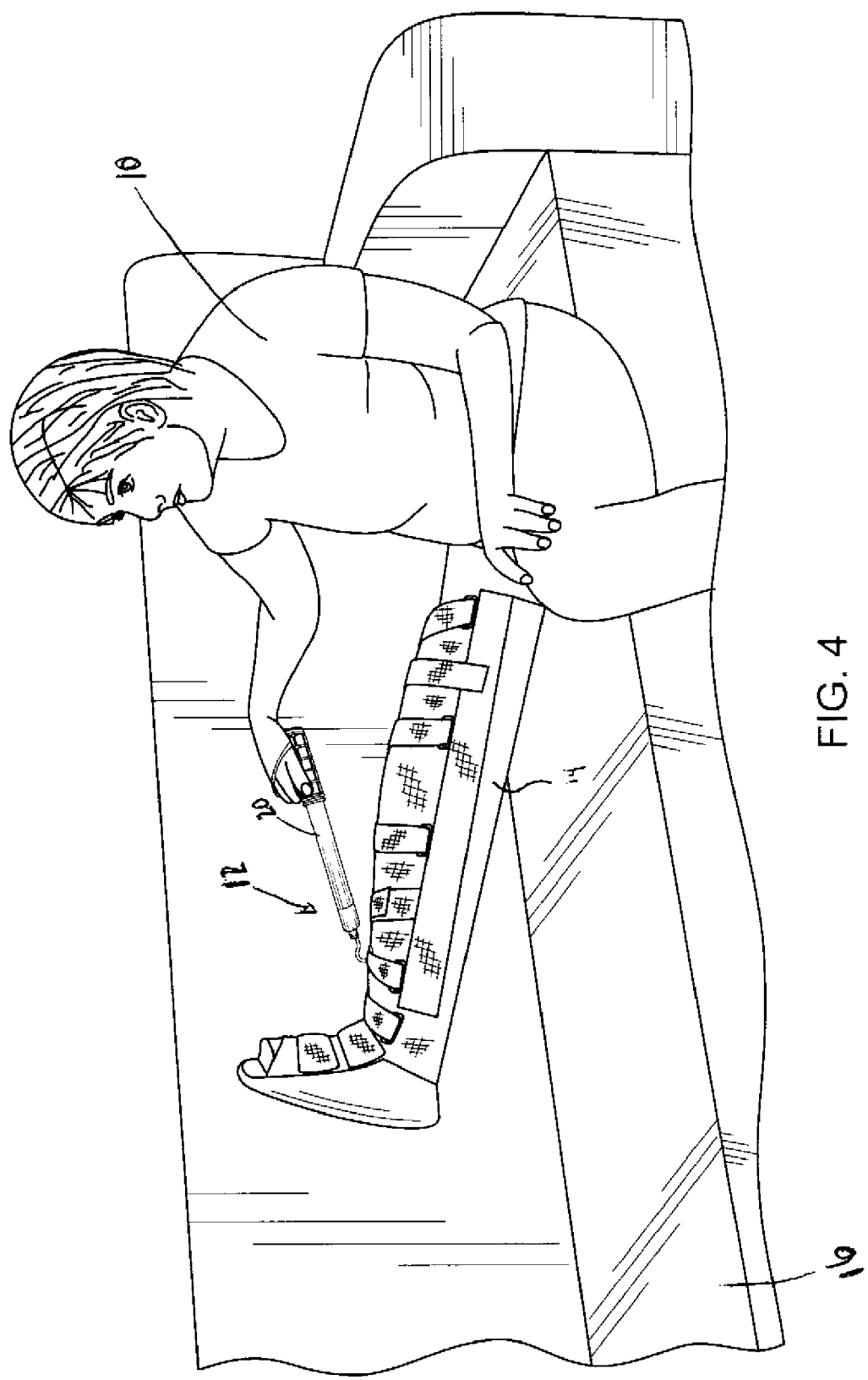
FIG. 4 illustrates lifting the leg up over the couch.
Figure 5:
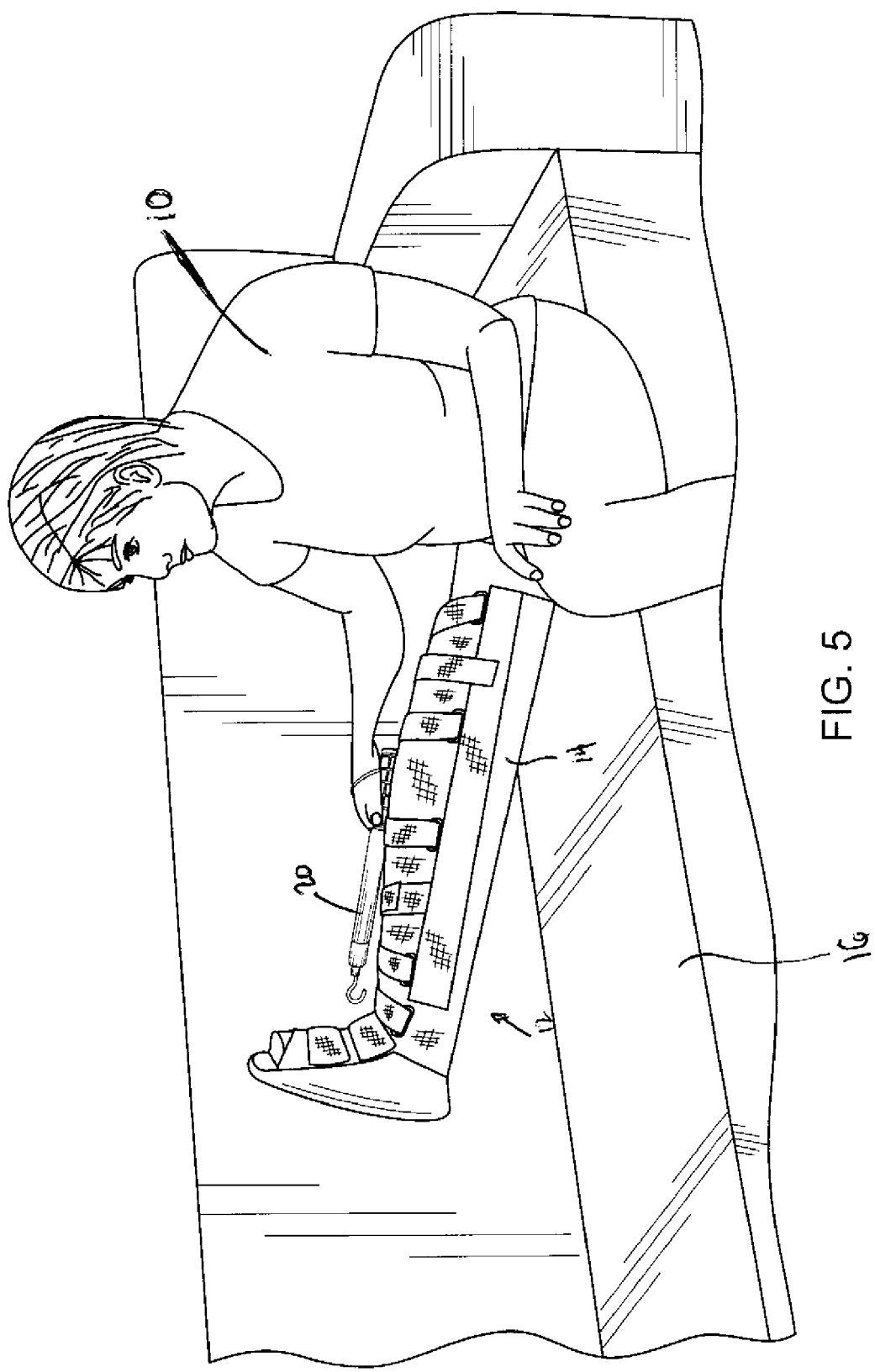
FIG. 5 illustrates releasing the device from the cast such that the leg may be positioned on the couch.

FIG. 2 illustrates the patient grasping the handle grip 26 of the device and reaching down to hook the hook 28 onto a portion of the cast (FIG. 3). In this case, the hook reaches the lower-most strap and is hooked thereon. The user can then move the leg up/down and side-to-side as desired. In FIG. 4, the patient has pulled the leg up to the level of the couch 16, then over to a position above the couch. The patient may then release the hook 28 once the leg is in a desired position. That position may be on the surface of the couch or, alternatively as in FIG. 5, the hook may be released when the leg is a short distance above the couch such that release can be made without the patient having to stretch or bend over, when appropriate.

Figure 10:
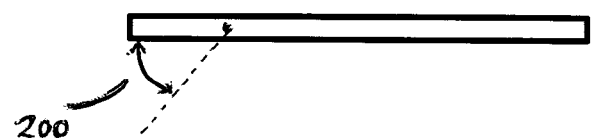
FIG. 10 illustrates a shaft embodiment with an adjustable angle distal end.

FIG. 6 illustrates one embodiment of a device 20 according to the present invention. The device includes a shaft 24, which may be made of wood, metal, a composite material, a polymer or any suitable material. The shaft may be solid or hollow. The shaft may be linear, or may be curved or otherwise shaped for particular uses, For example, the distal end may be angled to position the hook optimally for particular uses. In one embodiment, the angle 200 of the distal end is adjustable (FIG. 10) Optionally, the shaft may be covered with a film, such as a heat shrink wrap, that is colored, patterned, or otherwise ornamental. The film and handle grip may be the same color or compatible colors, and/or with coordinating patterns, to enhance aesthetic appearance.

The proximal end includes a grip 26, which in one embodiment is a resilient non-slip material. The grip may also be a bicycle-style grip. Optionally, the device may include an adjustable wrist strap 30 to help keep the device attached to the wrist during use. The distal end of the device includes a hook 28. The hook may be screwed directly into the shaft in the case of the shaft being a solid material such as wood. Alternatively, the hook may be provided on an assembly that is secured to the shaft. A resilient polymer cap 40 (FIG. 6) may be placed on the distal end of the shaft for aesthetic reasons and/or to smooth out the sharp edge of the distal end of the shaft.

FIG. 7 illustrates individual components of a device according to the present invention. In the embodiment of FIG. 7, the device includes a shaft, a handle grip to slide onto the proximal portion of the shaft. A hook 28 with a threaded portion is provided to screw into the end of the shaft 24. A film 32, such as heat shrink wrap, is represented. As previously noted, the film 32 may have a decorative pattern and/or color. The handle 26 may be colored and/or patterned as well, to be visually compatible with the shaft. Colored and/or pattern duct tape may also be used. Suitable shrink wrap material, duct tape and/or other wraps or coatings are known in the art.

As non-limiting exemplary dimensions, in one embodiment the shaft 24 is a dowel with a circular cross-section, made of wood such as oak, and is approximately 12 inches long and ⅞ inch in diameter. The hook may be ¾ inch stainless steel. The handle grip is 4 inches long, and the wrist strap loop is 9 inches long (that is, a length of cord that is 18 inches long, becoming 9 inches long when made into a loop). As just one example, the wrist strap loop may be ⅛ inch paracord. A dual drawstring locking device 42 may be used to adjust the wrist strap for a particular user.

In other embodiments, the shaft is a molded polymer, a hollow metal tube, or a metal rod, for example.

Figure 8A:
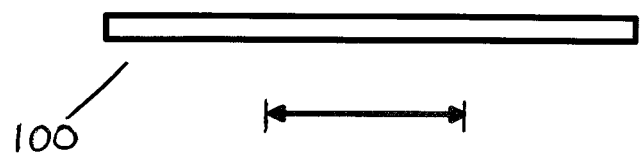
FIG. 8A illustrates a shaft of adjustable length in a longer configuration.
Figure 8B:
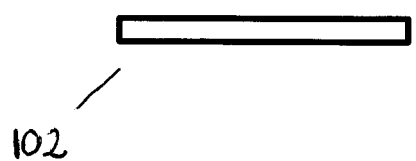
FIG. 8B illustrates the shaft of FIG. 8A in a shortened configuration.

Various options may be included in particular embodiments of the present invention. For example, in alternative embodiments, the shaft may be non-linear and be curved or otherwise provided with an advantageous shape. Although the length of the device is typically fixed; some embodiments may include a shaft that is variable in length. (FIGS. 8A, 8B In one example, the shaft is telescoping and the user adjusts the length as desired then locks the length into place. Details of telescoping adjustable shafts generally are known in the art.

Figure 9:
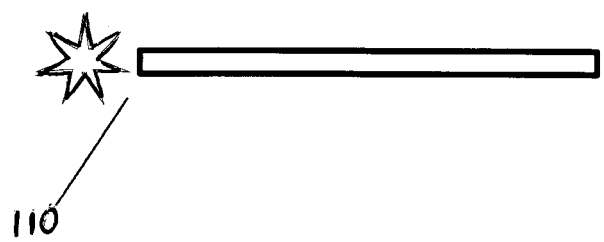
FIG. 9 illustrates an embodiment having a light source.

The device might also include, for example, a light source 110 (FIG. 9) such as an LED that the user may activate at night to better illuminate the area to be hooked. The LED may be interconnected to a button on the handle, for example, such that the user may switch it on and off. A power source such as a replaceable and/or rechargeable battery may be housed within the interior of the shaft, the handle, or elsewhere on the device as convenient.

The user is typically the patient. But alternatively, a nurse, physical therapist, or other may use the device to perform the steps in a method according to the present invention.

In view of the many possible embodiments to which the disclosed principles may be applied, it should be recognized that the illustrated embodiments are only preferred examples and should not be taken as limiting the scope of the disclosure. Rather, the scope is defined by the following claims. We therefore claim all that comes within the scope and spirit of these claims.

What is claimed is:

1. A method of repositioning an injured leg of a patient extending down from a surface, wherein the patient has a foot, ankle, and knee, the method comprising the steps of:
   grasping a handle grip of a repositioning device, the repositioning device comprising a straight solid wooden shaft at least 12 inches long, a bicycle handle resilient grip on a proximal end of and extending along a length of the straight solid wooden shaft, a resilient polymer cap on a distal end of the straight solid wooden shaft, a hook that has a threaded portion that is screwed into and extends from the distal end of the straight solid wooden shaft, an adjustable wrist strap at the proximal end of the straight solid wooden shaft, and a decorative outer layer over the straight solid wooden shaft;
   securing the hook to an orthopedic structure that extends about at least a portion of the injured leg, the hook being secured at a location on the orthopedic structure in between the patient's ankle and knee;
   pulling the repositioning device upwardly to raise the injured leg at least as high as the surface;
   positioning the injured leg into a desired position; and
   disengaging the hook from the orthopedic structure to leave the injured leg in a desired position on the surface;
   wherein the injured leg is raised without putting direct force on the foot and ankle.

2. A method as in claim 1, wherein the method comprises raising the injured leg above and over a bed surface, lowering the injured leg onto the bed surface, and releasing the hook from the orthopedic structure.

3. A method as in claim 1, wherein the patient performs the steps of claim 1 themselves.

4. A method as in claim 1, wherein the repositioning device includes a light source and the method includes activating the light source to illuminate at least a portion of the orthopedic structure.

5. A method as in claim 1, wherein someone other than the patient performs the steps of claim 1.

6. A method as in claim 1, wherein the step of positioning the injured leg comprises repositioning the injured leg from a position in which the injured leg hangs down from a surface to a position in which the injured leg rests upon the surface.

7. A method as in claim 1, wherein the distal end of the straight solid wooden shaft is angled.

* * * * *